(12) United States Patent
Wu et al.

(10) Patent No.: US 9,230,423 B2
(45) Date of Patent: Jan. 5, 2016

(54) DRINKING REMINDER APPARATUS AND METHOD

(71) Applicant: HON HAI PRECISION INDUSTRY CO., LTD., New Taipei (TW)

(72) Inventors: Shu-Kai Wu, New Taipei (TW); Hsiao-Ping Chiu, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 14/273,470

(22) Filed: May 8, 2014

(65) Prior Publication Data

US 2014/0340229 A1 Nov. 20, 2014

(30) Foreign Application Priority Data

May 14, 2013 (TW) .............................. 102116991 A

(51) Int. Cl.
*G08B 21/00* (2006.01)
*G08B 21/24* (2006.01)
*G06F 19/00* (2011.01)
*A47G 23/16* (2006.01)

(52) U.S. Cl.
CPC ................ *G08B 21/24* (2013.01); *A47G 23/16* (2013.01); *G06F 19/322* (2013.01); *G06F 19/3431* (2013.01); *G06F 19/3475* (2013.01); *A61J 1/1418* (2015.05); *A61J 7/0436* (2015.05)

(58) Field of Classification Search
CPC ..... G02F 1/008; A47G 23/16; G06F 19/3475; G06F 19/322; G06F 13/3431; G06F 19/3431
USPC ............. 340/603, 309.8; 128/921; 206/459.1; 215/230, 387; 434/247
See application file for complete search history.

(56) References Cited

U.S. PATENT DOCUMENTS

| 5,644,298 A | 7/1997 | Brooks et al. |
| 5,673,691 A * | 10/1997 | Abrams et al. ................ 434/247 |
| 5,896,990 A * | 4/1999 | Barzana ..................... 206/459.1 |
| 6,252,494 B1* | 6/2001 | Howell ....................... 340/309.8 |
| 6,253,688 B1* | 7/2001 | Lor ............................... 108/132 |
| 6,588,593 B2* | 7/2003 | Woskoski .................. 206/459.1 |
| 7,851,775 B2* | 12/2010 | Hoyt et al. .................... 250/577 |
| 7,959,023 B2* | 6/2011 | Ferrara ......................... 215/230 |
| 7,959,567 B2* | 6/2011 | Stivoric et al. ................ 600/300 |
| 8,051,997 B2* | 11/2011 | Buckley ........................ 215/230 |
| 8,158,084 B2* | 4/2012 | Rinker et al. ................. 422/521 |
| 8,378,830 B2* | 2/2013 | Moran ........................ 340/573.1 |
| 2005/0229699 A1* | 10/2005 | Chai et al. ................... 73/304 R |
| 2006/0278156 A1 | 12/2006 | Miller |

\* cited by examiner

*Primary Examiner* — John A Tweel, Jr.
(74) *Attorney, Agent, or Firm* — Novak Druce Connolly Bove + Quigg LLP

(57) ABSTRACT

A drinking reminder method is implemented by an electronic apparatus. The apparatus includes a scale pan, a weight sensor, an analog/digital (A/D) converter, a display screen and a keypad. The keypad includes a power key, a reset key and a switching key. The weight sensor senses an analog pressure signal when a cup filled with water is placed on the scale pan, and the A/D converter converts the analog pressure signal to a digital weight signal. A total weight of the cup filled with water is measured according to the digital weight signal, and a cumulative water intake volume and a water shortage volume of a user. The display screen displays the cumulative water intake volume and the water shortage volume to remind the user to drink water.

18 Claims, 4 Drawing Sheets

| Step | Action | Cumulative water intake volume | Water shortage volume | Current water intake volume | Weight of a cup |
|---|---|---|---|---|---|
| 1 | Placing a cup filled with water on a scale pan to get a first measurement | $C_1$ | $L_1=2000$ | $C_1=0$ | $D_1$ |
| 2 | Placing the cup filled with water on the scale Pan to get a second measurement after drinking water | $\sum_{i=1}^{2} C_i$ | $L_2=2000-\sum_{i=1}^{2} C_i$ ($\sum_{i=1}^{2} C_i < 2000$) | $C_2=D_1-D_2$ | $D_2$ |
| 3 | Placing the cup filled with water on the scale Pan to get a third measurement after drinking water | $\sum_{i=1}^{3} C_i$ | $L_3=2000-\sum_{i=1}^{3} C_i$ ($\sum_{i=1}^{3} C_i < 2000$) | $C_3=D_2-D_3$ | $D_3$ |
| 4 | Placing the cup filled with water on the scale Pan to get a forth measurement after a reset key is pressed | $\sum_{i=1}^{4} C_i$ | $L_4=2000-\sum_{i=1}^{4} C_i$ ($\sum_{i=1}^{4} C_i < 2000$) | $C_4=0$ | $D_4$ |
| 5 | Placing the cup filled with water on the scale Pan to get a fifth measurement after drinking water | $\sum_{i=1}^{5} C_i$ | $L_5=2000-\sum_{i=1}^{5} C_i$ ($\sum_{i=1}^{5} C_i < 2000$) | $C_5=D_4-D_5$ | $D_5$ |
| ... | ... | | | | ... |
| n | Placing the cup filled with water on the scale Pan to get a nth measurement after drinking water | $\sum_{i=1}^{n} C_i$ | $L_n=0$ ($\sum_{i=1}^{n} C_i \geq 2000$) | $C_n=D_{n-1}-C_n$ | $D_n$ |

FIG. 4

DRINKING REMINDER APPARATUS AND METHOD

FIELD

The present disclosure relates to water reminder systems and methods, and particularly to a drinking water reminder apparatus and method that monitors information of user habits of drinking water.

BACKGROUND

According to the general standard of daily water intake recommended by medical professionals, most people do not drink enough water and are usually in a slightly dehydrated state due to personal living habits, and thus can be uncomfortable. At present, most drinking water reminders available in the market are used to determine whether or not sufficient water is taken by counting the number of cups of water being taken per day or reading the scales marked on a container. However, people still may forget how many number of cups of water has been taken every day.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

FIG. 4 is a schematic diagram of an example embodiment of a cumulative water intake and a water shortage in every day.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean "at least one."

In the present disclosure, the word "module," refers to logic embodied in hardware or firmware, or to a collection of software instructions, written in a program language. In one embodiment, the program language may be Java, C, or assembly. One or more software instructions in the modules may be embedded in firmware, such as in an EPROM. The modules described herein may be implemented as either software and/or hardware modules and may be stored in any type of non-transitory computer-readable media or storage medium. Some non-limiting examples of a non-transitory computer-readable medium comprise CDs, DVDs, flash memory, and hard disk drives.

Figure 1:
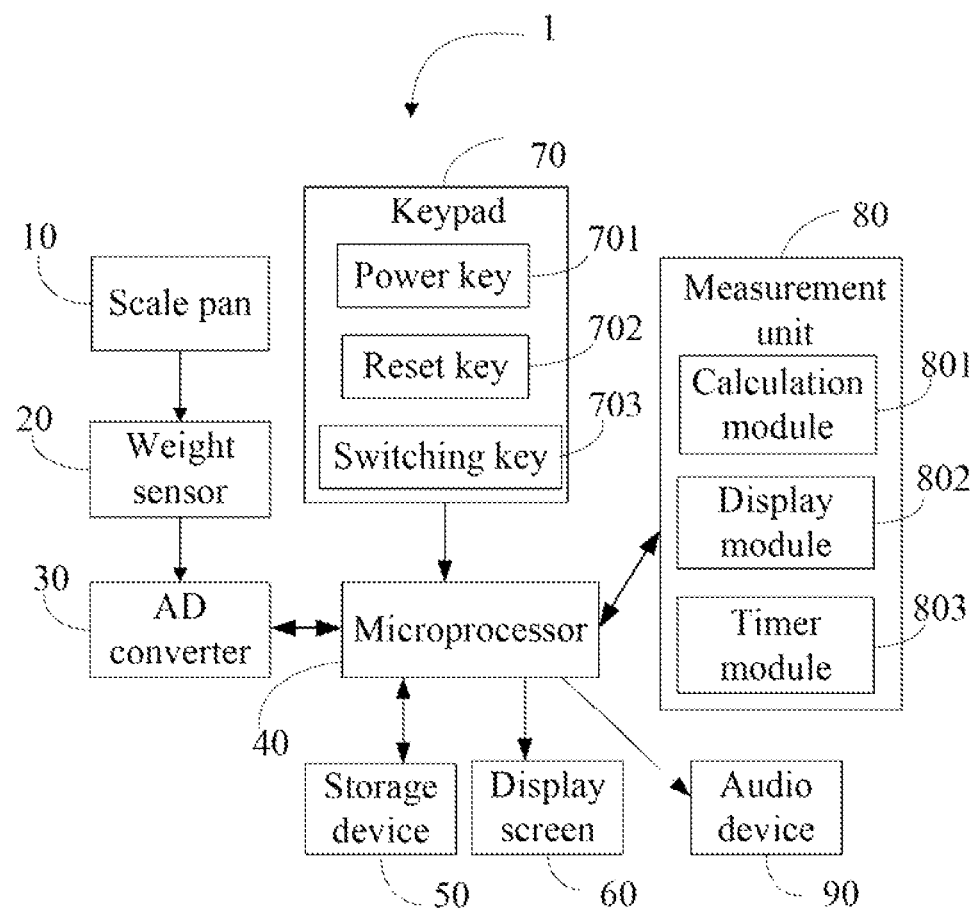
FIG. 1 illustrates a block diagram of one embodiment of a drinking reminder apparatus.

FIG. 1 illustrates a block diagram of one embodiment of a drinking reminder apparatus 1. In the embodiment, the drinking reminder apparatus 1 includes a scale pan 10, a weight sensor 20, an analog/digital (A/D) converter 30, a microprocessor 40, a storage system 50, a display screen 60, a keypad 70, a measurement unit 80, and an audio device 90. The microprocessor 40 connects to each component through a respective electronic line, and communicates with each component. FIG. 1 illustrates only one example of the drinking reminder apparatus 1, and other examples can comprise more or fewer components than those shown in the embodiment, or have a different configuration of the various components.

The weight sensor 20 senses an analog pressure signal when a cup is placed on the scale pan 10, and sends the analog pressure signal to the A/D converter 30. In the embodiment, the analog pressure signal is represented by pressure waves that are generated by the weight sensor 20. The A/D converter 30 converts the analog pressure signal to a digital weight signal, and sends to the digital weight signal to the microprocessor 40.

The at least one microprocessor 40 can be a central processing unit (CPU), a microprocessor, or other suitable data processor chip that performs various functions of the drinking reminder apparatus 1. In one embodiment, the storage device 50 can be an internal storage system, such as a flash memory, a random access memory (RAM) for temporary storage of information, and/or a read-only memory (ROM) for permanent storage of information. The storage device 50 can also be an external storage system, such as an external hard disk, a storage card, or a data storage medium.

The keypad 70 includes, but is not limited to, a power key 701, a reset key 702, and a switching key 703. The power key 701 is configured to power on or power off the drinking reminder apparatus 1 when the power key 701 is pressed. The reset key 702 is configured to reset a water intake of a user when the reset key 702 is pressed. The switching key 703 is configured to display a cumulative water intake or a current water shortage of the user on the display screen 60 when the switching key 703 is pressed. The audio device 90 generates a voice message to remind the user to drink enough water.

In one embodiment, the measurement unit 80 comprises, but is not limited to, a calculation module 801, a display module 802, and a timer module 803. The modules 801-803 can comprise computerized instructions in the form of one or more computer-readable programs that can be stored in a non-transitory computer-readable medium, for example the storage device 50, and executed by the at least one microprocessor 40 of the drinking reminder apparatus 1.

Figure 2:
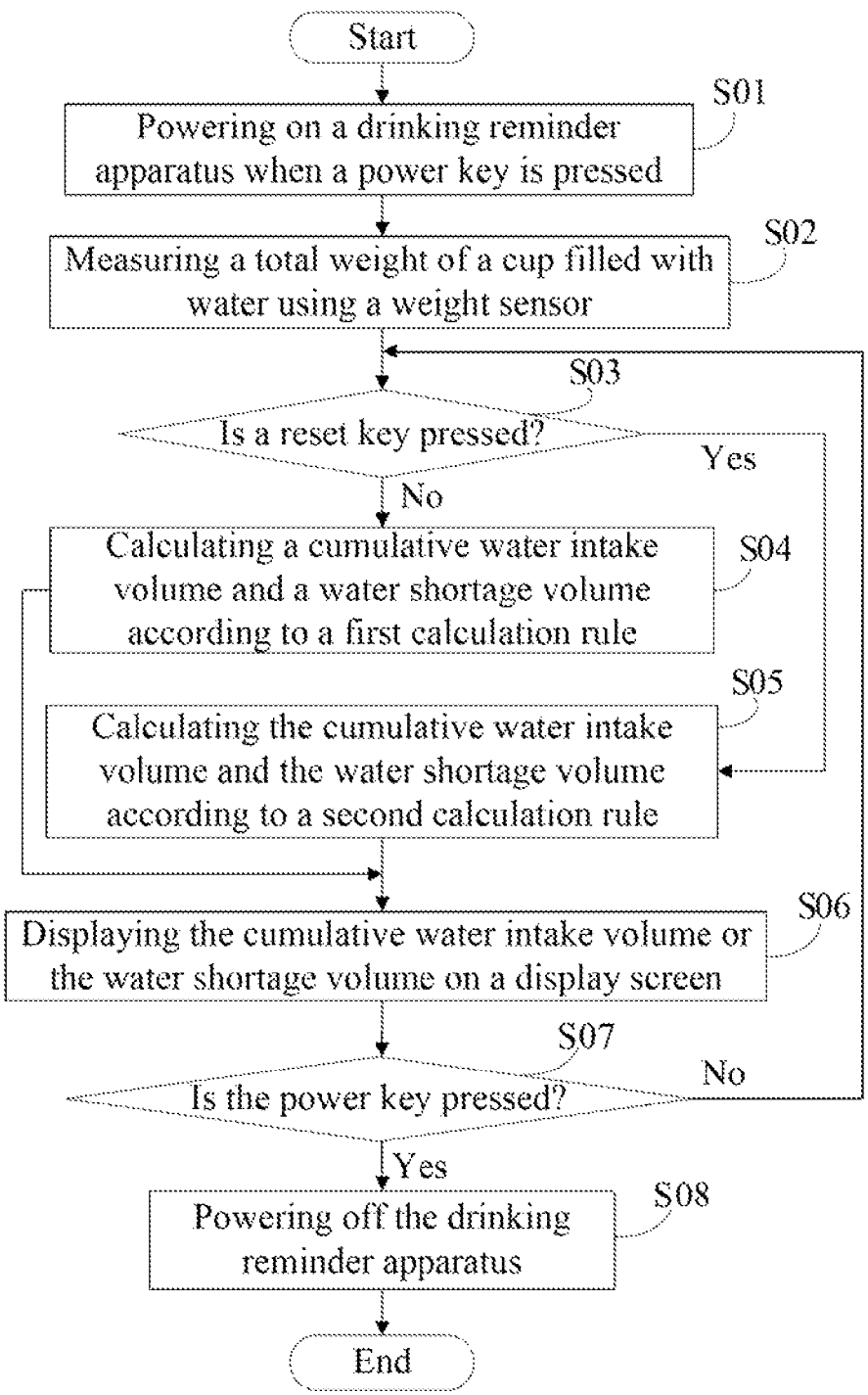
FIG. 2 illustrates a flowchart of one embodiment of a drinking reminder method.

FIG. 2 illustrates a flowchart of one embodiment of a drinking reminder method. In an example embodiment, the method is performed by execution of computer-readable software program codes or instructions by at least one microprocessor of an electronic apparatus, such as the drinking reminder apparatus 1 of FIG. 1. Depending on the embodiment, additional blocks may be added, others removed, and the ordering of the blocks may be changed.

In block SOL the drinking reminder apparatus 1 is powered on when the power key 701 is pressed. In the embodiment, the drinking reminder apparatus 1 can be equipped with one or more batteries or can be connected to a power supply to provide power for the drinking reminder apparatus 1.

In block S02, the weight sensor 20 senses an analog pressure signal when a cup filled with water is placed on the scale pan 10, the A/D converter 30 converts the analog pressure signal to a digital weight signal, and the calculation module 801 measures a total weight of the cup filled with water according to the digital weight signal. In the embodiment, the calculation module 801 further initializes a plurality of parameters comprising a current water intake, a cumulative water intake, and a current water shortage of a user. For example, the current water intake $C_1$ is initialized as zero, the cumulative water intake $S_1$ is initialized as zero, and the current water shortage is initialized as L=2000 CC (cubic centimeter), wherein L represents a daily standard volume of drinking water intake by the user.

In the embodiment, the weight of the cup filled with water equals the weight of the cup plus the weight of the water filled in the cup. The current water intake equals the previous weight of the cup filled with water minus the current weight of the cup filled with water. The cumulative water intake equals the previous cumulative water intake plus the current water intake. The current water shortage equals the daily standard volume minus the cumulative water intake. In one example with respect to FIG. 4, if the current water intake is denoted as $C_1$, the cumulative water intake $S_1=C_1$, and the current water shortage L=2000 CC. It is understood that the density ρ of water may approximate to 1.0, the current water intake $C_1$, the cumulative water intake $S_1$, and the current water shortage L can be represented by a weight unit according to an equation m=ρv.

Figure 3:
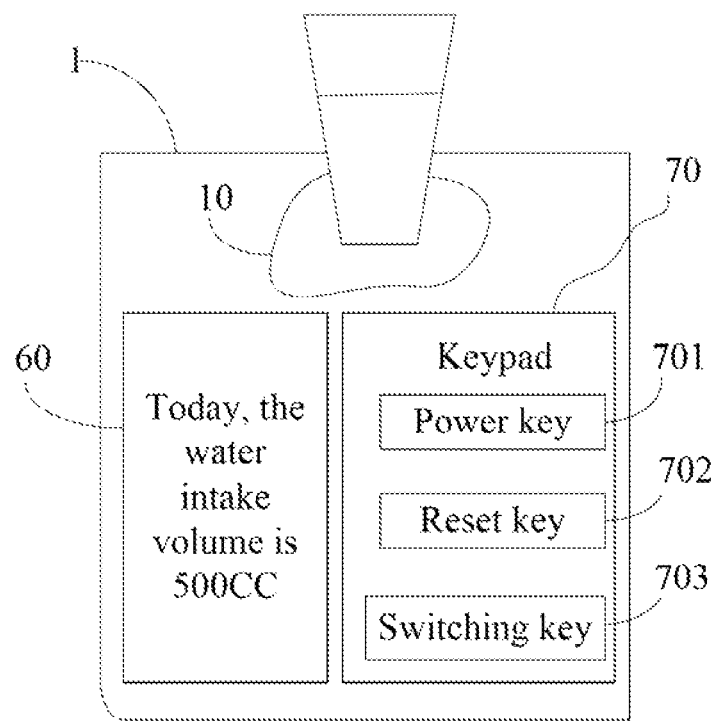
FIG. 3 is a schematic diagram of an example embodiment of measuring weight of a cup filled with water.

In block S03, the calculation module 801 determines whether the reset key 702 is pressed when the cup filled with water is placed on the scale pan 10 every time. Referring to FIG. 3, when the cup is refilled with water after drinking water of the cup, the reset key 702 should be pressed to reset the water monitor parameters. If the reset key 702 is not pressed, block S04 is implemented. Otherwise, if the reset key 702 is not pressed, block S05 is implemented.

In block S04, the calculation module 801 calculates a cumulative water intake volume and a water shortage volume according to a first calculation rule and the weight of the cup filled with water. In the embodiment, the first calculation rule is described as: the cumulative water intake volume equals the previous cumulative water intake volume plus the current water intake volume, and the water shortage volume equals the daily standard volume minus the cumulative water intake volume. If the cumulative water intake volume is less than 2000 CC, the water shortage volume is equal to 2000 CC subtracted from the cumulative water intake volume. If the cumulative water intake volume is not less than 2000 CC, the water shortage volume is equal to zero. In one example with respect to FIG. 4, if the previous weight of the cup filled with water is denoted as $D_1$, and the current cup filled with water is denoted as $D_2$. The current water intake volume $C_2=D_2-D_1$, and the cumulative water intake volume $$S_2 = \sum_{i=1}^{2} Ci,$$

and the water shortage volume L=2000 CC$-S_2$.

In block S05, the calculation module 801 calculates the cumulative water intake volume and the water shortage volume according to a second calculation rule and the weight of the cup filled with water. In the embodiment, the second calculation rule is denoted as: the current water intake volume equals 0, the cumulative water intake volume equals the previous cumulative water intake volume, and the water shortage volume equals the daily standard volume minus the cumulative water intake volume. If the cumulative water intake volume is less than 2000 CC, the water shortage volume equals 2000 CC subtracted from the cumulative water intake volume. If the cumulative water intake volume is not less than 2000 CC, the water shortage volume is equal to zero. In one example with respect to FIG. 4, if the previous weight of the cup filled with water is denoted as $D_4$, and the current cup filled with water is denoted as $D_5$. The current water intake volume $C_5=D_5-D_4$, and the cumulative water intake volume $$S_5 = \sum_{i=1}^{5} Ci,$$

i.e., $S_5=S_4+C_5$, (under $S_5$ circumstances $S_4=S_5$), and the water shortage volume L=2000 CC$-S_5$.

In block S06, the display module 802 displays the cumulative water intake volume or the water shortage volume on the display screen 60 to remind the user to drink water. Referring to FIG. 3, the display screen 60 displays information of the cumulative water intake volume, for example 500 CC, and the water shortage volume, for example, 1500 CC.

In block 507, the timer module 803 detects whether the power key 701 is pressed. If the power key 701 is pressed, block S08 is implemented. Otherwise, if the power key 701 is not pressed, the process returns to block S03 as described above.

In block S08, the timer module 803 controls the drinking reminder apparatus 1 to power off when the power key 701 is pressed.

In the embodiment, the timer module 803 can set a first time interval to implement a save power function of the drinking reminder apparatus 1, and can also set a second time interval to implement a prompt function of the drinking reminder apparatus 1. The first time interval is less than the second time interval, for example, the first time interval can be set as 10 minutes, and the second time interval can be set as 30 minutes. The timer module 803 starts to count a time period every time when the cup is placed on the scale pan 10. If the time period is equal to the first time interval, the timer module 803 powers off the display screen 60 to save power consumption of the drinking reminder apparatus 1, and continues to count the time period. If the time period is equal to the second time interval, the timer module 803 powers on the display screen 60 to display the cumulative water intake volume and the water shortage volume, and controls the audio device 90 to send a voice message to remind the user to drink water. For example, the cumulative water intake volume is 500 CC, please drink water to supplement daily water intake volume in time.

All of the processes described above may be embodied in, and fully automated via, functional code modules executed by one or more general purpose processors of electronic devices. The code modules may be stored in any type of non-transitory readable medium or other storage device. Some or all of the methods may alternatively be embodied in specialized hardware. Depending on the embodiment, the non-transitory readable medium may be a hard disk drive, a compact disc, a digital video disc, a tape drive or other suitable storage medium.

Although certain disclosed embodiments of the present disclosure have been specifically described, the present disclosure is not to be construed as being limited thereto. Various changes or modifications may be made to the present disclosure without departing from the scope and spirit of the present disclosure.

What is claimed is:

1. A drinking reminder apparatus, comprising:
   a scale pan, a weight sensor, an analog/digital (A/D) converter, a display screen and a keypad comprising a power key, and a reset key; and
   a storage device storing a computer-readable program comprising instructions that, when executed by at least one microprocessor, causes the at least one microprocessor to:

sense an analog pressure signal using the weight sensor when a cup filled with water is placed on the scale pan;
convert the analog pressure signal to a digital weight signal using the A/D converter;
measure a total weight of the cup filled with water according to the digital weight signal;
determine whether the reset key is pressed when the cup filled with water is placed on the scale pan;
calculate a cumulative water intake volume and a water shortage volume of a user according to a first calculation rule and the total weight of the cup filled with water if the reset key is not pressed;
calculate the cumulative water intake volume and the water shortage volume according to a second calculation rule and the total weight of the cup filled with water if the reset key is pressed; and
display the cumulative water intake volume or the water shortage volume on the display screen to remind the user to drink water.

2. The apparatus according to claim 1, further comprising an audio device for generating a voice message to remind the user of drinking water in time.

3. The apparatus according to claim 2, wherein the computer-readable program further causes the at least one microprocessor to:
set a first time interval and a second time interval, the first time interval being less than the second time interval;
start to count a time period at every time when the cup is placed on the scale pan;
power off the display screen to save power consumption of the drinking reminder apparatus when a time period equal to the first time interval has elapsed; and
power on the display screen to display the cumulative water intake volume and the water shortage volume when a time period equal to the second time interval has elapsed, and control the audio device to generate the voice message to remind the user drinking water.

4. The apparatus according to claim 1, wherein the first calculation rule is defined as:
the cumulative water intake volume equals a previous cumulative water intake volume plus a current water intake volume; and
the water shortage volume equals a daily standard volume minus the cumulative water intake volume.

5. The apparatus according to claim 1, wherein the second calculation rule is defined as:
the current water intake volume equals 0, and the cumulative water intake volume equals a previous cumulative water intake volume; and
the water shortage volume equals a daily standard volume minus the cumulative water intake volume.

6. The apparatus according to claim 1, wherein the keypad further comprises a switching key, and the display screen displays the cumulative water intake volume or the water shortage volume when the switching key is pressed.

7. A drinking reminder method being executed by at least one microprocessor of an electronic apparatus, the electronic apparatus comprising a scale pan, a weight sensor, an analog/digital (A/D) converter, a display screen and a keypad comprising a power key and a reset key, the method comprising:
sensing an analog pressure signal using the weight sensor when a cup filled with water is placed on the scale pan;
converting the analog pressure signal to a digital weight signal using the A/D converter;
measuring a total weight of the cup filled with water according to the digital weight signal;
determining whether the reset key is pressed when the cup filled with water is placed on the scale pan;
calculating a cumulative water intake volume and a water shortage volume of a user according to a first calculation rule and the total weight of the cup filled with water if the reset key is not pressed;
calculating the cumulative water intake volume and the water shortage volume according to a second calculation rule and the total weight of the cup filled with water if the reset key is pressed; and
displaying the cumulative water intake volume or the water shortage volume on the display screen to remind the user to drink water.

8. The method according to claim 7, wherein the electronic apparatus further comprises an audio device for generating a voice message to remind the user of drinking water in time.

9. The method according to claim 8, further comprising:
setting a first time interval and a second time interval, the first time interval being less than the second time interval;
starting to count a time period at every time when the cup is placed on the scale pan;
powering off the display screen to save power consumption of the drinking reminder apparatus when a time period equal to the first time interval has elapsed; and
powering on the display screen to display the cumulative water intake volume and the water shortage volume when a time period equal to the second time interval has elapsed, and controlling the audio device to generate the voice message to remind the user drinking water.

10. The method according to claim 7, wherein the first calculation rule is defined as:
the cumulative water intake volume equals a previous cumulative water intake volume plus a current water intake volume; and
the water shortage volume equals a daily standard volume minus the cumulative water intake volume.

11. The method according to claim 7, wherein the second calculation rule is defined as:
the current water intake volume equals 0, and the cumulative water intake volume equals a previous cumulative water intake volume; and
the water shortage volume equals a daily standard volume minus the cumulative water intake volume.

12. The method according to claim 7, wherein the keypad further comprises a switching key, and the display screen displays the cumulative water intake volume or the water shortage volume when the switching key is pressed.

13. A non-transitory storage medium having stored thereon instructions that, when executed by at least one microprocessor of an electronic device, causes the least one microprocessor to perform a drinking reminder method, the electronic apparatus comprising a scale pan, a weight sensor, an analog/digital (A/D) converter, a display screen and a keypad comprising a power key and a reset key, the method comprising:
sensing an analog pressure signal using the weight sensor when a cup filled with water is placed on the scale pan;
converting the analog pressure signal to a digital weight signal using the A/D converter;
measuring a total weight of the cup filled with water according to the digital weight signal;
determining whether the reset key is pressed when the cup filled with water is placed on the scale pan;
calculating a cumulative water intake volume and a water shortage volume of a user according to a first calculation rule and the total weight of the cup filled with water if the reset key is not pressed;

calculating the cumulative water intake volume and the water shortage volume according to a second calculation rule and the total weight of the cup filled with water if the reset key is pressed; and displaying the cumulative water intake volume or the water shortage volume on the display screen to remind the user to drink water.

14. The storage medium according to claim 13, wherein the electronic apparatus further comprises an audio device for generating a voice message to remind the user of drinking water in time.

15. The storage medium according to claim 14, further comprising:

setting a first time interval and a second time interval, the first time interval being less than the second time interval;

starting to count a time period at every time when the cup is placed on the scale pan;

powering off the display screen to save power consumption of the drinking reminder apparatus when a time period equal to the first time interval has elapsed; and powering on the display screen to display the cumulative water intake volume and the water shortage volume when a time period equal to the second time interval has elapsed, and controlling the audio device to generate the voice message to remind the user drinking water.

16. The storage medium according to claim 13, wherein the first calculation rule is defined as:

the cumulative water intake volume equals a previous cumulative water intake volume plus a current water intake volume; and the water shortage volume equals a daily standard volume minus the cumulative water intake volume.

17. The storage medium according to claim 13, wherein the second calculation rule is defined as:

the current water intake volume equals 0, and the cumulative water intake volume equals a previous cumulative water intake volume; and the water shortage volume equals a daily standard volume minus the cumulative water intake volume.

18. The storage medium according to claim 13, wherein the keypad further comprises a switching key, and the display screen displays the cumulative water intake volume or the water shortage volume when the switching key is pressed.

* * * * *